US00PP31769P2

(12) United States Plant Patent
Carrera et al.

(10) Patent No.: US PP31,769 P2
(45) Date of Patent: May 19, 2020

(54) LEMON TREE NAMED 'GLUECK'

(50) Latin Name: *Citrus limon*
Varietal Denomination: Glueck

(71) Applicant: Citromax Group, Inc., Carlstadt, NJ (US)

(72) Inventors: Fernando José Maria Carrera, Monteros (AR); Raúl Eduardo Tan Jun Roldán, Monteros (AR); Cristian Viruel, Monteros (AR)

(73) Assignee: CITROMAX GROUP, INC., Carlstadt, NJ (US)

( * ) Notice: Subject to any disclaimer, the term of this patent is extended or adjusted under 35 U.S.C. 154(b) by 0 days.

(21) Appl. No.: 16/350,581

(22) Filed: Dec. 3, 2018

(51) Int. Cl.
*A01H 5/00* (2018.01)
*A01H 6/78* (2018.01)

(52) U.S. Cl.
USPC ..... Plt./201

(58) Field of Classification Search
USPC ..... Plt./201
CPC ..... A01H 5/00; A01H 6/78
See application file for complete search history.

(56) References Cited

U.S. PATENT DOCUMENTS

| | | | |
|---|---|---|---|
| PP25,531 | P2 | 5/2015 | Moy et al. |
| PP27,745 | P3 | 3/2017 | Grosser |
| PP29,265 | P3 | 5/2018 | Silva |
| PP29,300 | P3 | 5/2018 | Park et al. |

OTHER PUBLICATIONS

Bitters, W.P. "Citrus Rootstocks: Their Characters and Reactions." an unpublished manuscript, ca. 1986.

*Primary Examiner* — Annette H Para
(74) *Attorney, Agent, or Firm* — Jondle & Associates, P.C.

(57) ABSTRACT

A new and distinct variety of lemon named 'Glueck' characterized by producing mature fruit with a juice having a lemon flavor and a high sugar-acid ratio.

21 Drawing Sheets

Latin name of the genus and species of the plant claimed: *Citrus limon.*

Varietal denomination: 'Glueck'.

BACKGROUND OF THE NEW VARIETY

The present invention refers to a new variety of lemon which will hereinafter be denominated as the 'Glueck' lemon tree. The 'Glueck' lemon tree produces lemon fruit that taste like lemon, but have juice with a high sugar-acid ratio, producing a lemon flavor without the sourness associated with lemon juice.

ORIGIN AND ASEXUAL REPRODUCTION OF THE NEW VARIETY

The invention (variety) comprises a new and distinct variety of a lemon tree discovered by the inventors in a cultivated orchard on the Finca Los Pocitos property in the Tucumán province of Argentina, which was purchased in 1993, and subsequently continuously owned, by the Applicant. Specifically, while working on the Finca Los Pocitos property, the inventors discovered the new cultivar and scion buds were removed from the identified trees for grafting onto Troyer citrange "Troy" rootstock (unpatented), which is a hybrid of *Citrus sinensis* and *Poncirus trifoliate*, to form a second generation. The new cultivar is believed to a spontaneous mutation of a lemon tree grown in the cultivated orchard. From the second generation, trees were selected on the basis of fruit superiority and growth parameters and scion buds were removed from the selected trees for further asexual reproduction by grafting to form a third generation. The new cultivar was subsequently asexually reproduced by the inventors in the Tucumán province of Argentina by grafting on a variety of root stocks, including Citrumelo Swingle CPB 4475 (*Poncirus trifoliata* x *Citrus paradisi*), Citrange C-35 (*Citrus sinensis* 'Ruby' orange x X *Citroncirus webberii* 'Webber-Fawcett' trifoliata), and 79 AC (*Citrus reshni* Hort. ex Tan. x *Citrus paradisi* Macf. x *Poncirus trifoliata* (L.) Raf.). This year the new cultivar was also grafted on *Poncirus trifoliata* 'Rubidoux' and Flying Dragon (*Poncirus trifoliata* var. 'Monstrosa') root stock. The inventors carefully compared all of the asexually reproduced trees with the originally discovered trees and found the fruit to be substantially identical in all distinctive respects through several generations of asexual reproduction including on different root stocks. The discovered cultivar has been shown to remain true to type in successive generations of such asexual reproductions.

In comparison with conventional lemon trees, the fruit of the present variety has a higher sugar-acid ratio, resulting in a fruit having a juice with a lemon flavor but lacking the sour acidity associated with typical lemon fruits.

SUMMARY OF THE NEW VARIETY

The 'Glueck' lemon tree is particularly characterized by producing fruit with a high sugar-acid ratio, with a fall of fruits in December, with good fruit size.

DETAILED BOTANICAL DESCRIPTION

Figure 1:
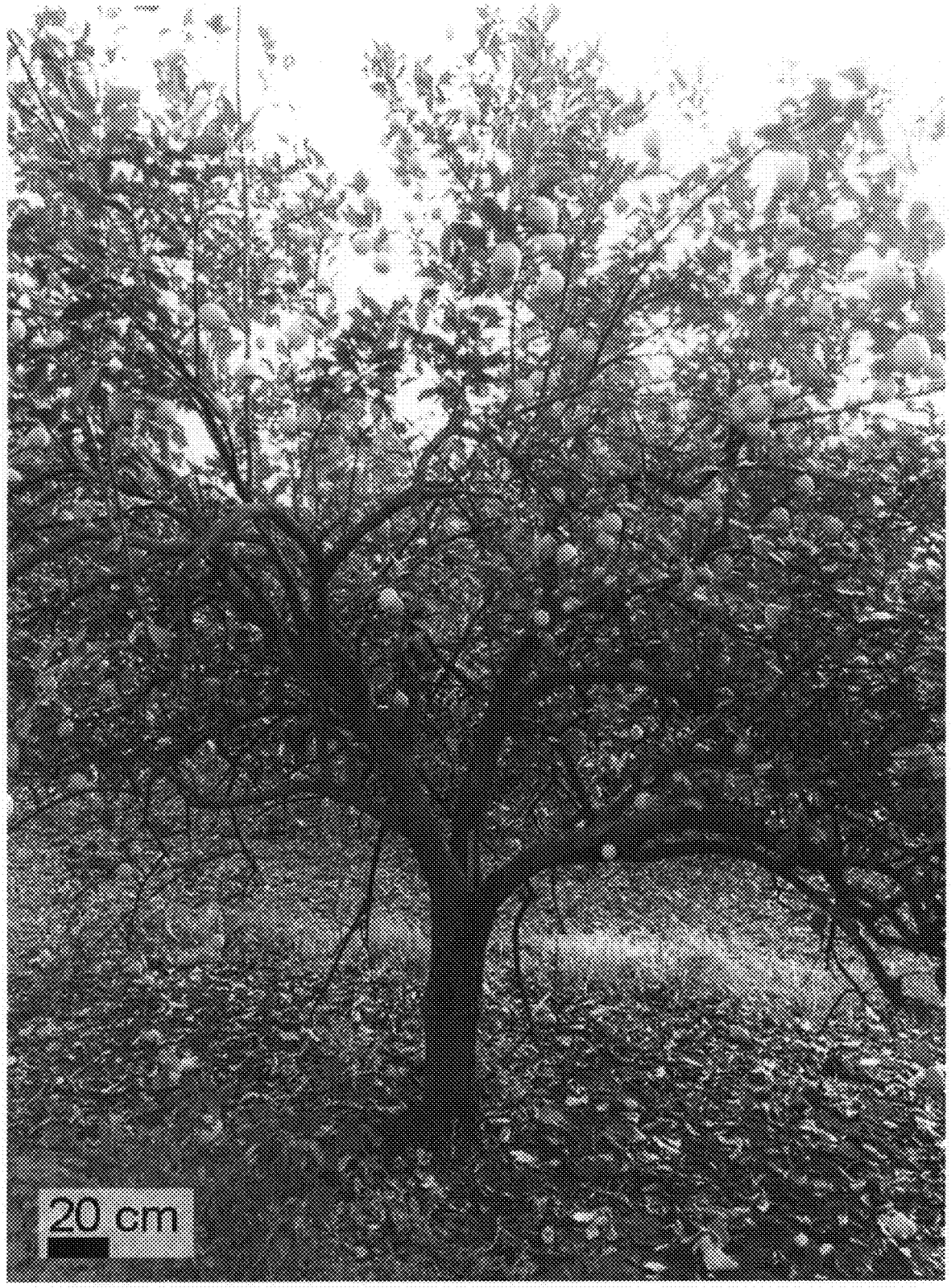
FIG. 1 is a color photograph of the general appearance of the plants.

It should be noted that the described characteristics may vary depending on agricultural practices and climatic conditions, location and season. The quantitative values set forth below are expressed as an average value, which is obtained from the specimens analyzed. Quantitative traits were taken from each of four specimen trees. The angles of divergence of the fruit branches with respect to the main axis were calculated by means of scale photographs.

Twenty fully developed leaves were selected from each specimen, considering the fifth leaf from the apex in orientation N, S, E, W and in good phytosanitary conditions. They were measured and photographed with a digital camera to calculate quantitative data. To determine the venation, size, and density of essential oil glands, the diaphanization and clarification technique was performed according to C. Dizeo de Strittmatter, "Nueva técnica de diafanización," Bol. Soc. Arg. Bot. 15, 126-129 (1973) and later stained with 1% cresyl violet, as per G. E. Zarlaysky, "Histologia vegetal: técnicas simples y complejas," 1a ed. Sociedad Argentina de Botánica, Buenos Aires (2014).

Ten flower buds were taken from each specimen in development stage medium and ten flowers in were taken in maturity stage (open corolla). These were measured and photographed to calculate quantitative values.

All observations of fruits and their parts were made at the optimum maturity stage. The characteristics described below correspond to the average of ten fruits and their respective seeds of each specimen.

Quantitative values were calculated directly through the use of calibrated measuring tape (TJIMA 30 m) and vernier caliper using scale photographs (made with a KODAK digital camera Az-252 16 mpx). Micromorphological values, surfaces, and angles were calculated using a Zeiss Stemi-2000C stereo microscope with a Zeiss Axiocam ERc 5s digital camera attached and AxioVision software version 4.8.2 (Carl Zeiss Ltd, Herts, UK). All values are expressed as mean values and standard deviation.

The descriptions of foliar traits and shapes were made following B. D. Ellis, C. Daly, L. J. Hickey, H. R. Johnson, J. D. Mitchell, P. Wilf, S. L. Wing, "Manual of leaf architecture," Cornell University Press, USA (2009)

The colors are described in reference to The 2005 Royal Horticultural Society mini color chart.

The determination of sugars and acidity in juice was carried out in concentrated juice (10 mL) for each specimen by titration with 0.1 N sodium hydroxide and 1% phenolphthalein. The specifications by the Department of Primary Industries and Regional Development Agriculture and Food of the Government of Australia were followed.

The titration was monitored by color change and pH change up to 8.2-8.4.

Phenotypic Description of *Citrus limon* 'Glueck'.

Tree:

*Size*.—Medium size. Height: 4.19±0.13 m high (0.25 to 0.35 m corresponding to the Troy rootstock) Width: 6.06±0.53 m wide at the crown level.

*Vigor*.—Specimens are medium-vigor mature trees, the presence of aphids and leaf spots is detected. Tolerance to winter conditions and drought are expected to be the same as those of the rootstock.

*Flowering*.—First flowering occurs in August and full flowering in September, while the fall of fruits is expected for December.

Trunk:

*Size*.—Rootstock has a diameter of 0.60±0.02 cm and a trunk 0.58±0.04 cm in diameter, 30 cm above the rootstock (FIG. 1).

Figure 2:
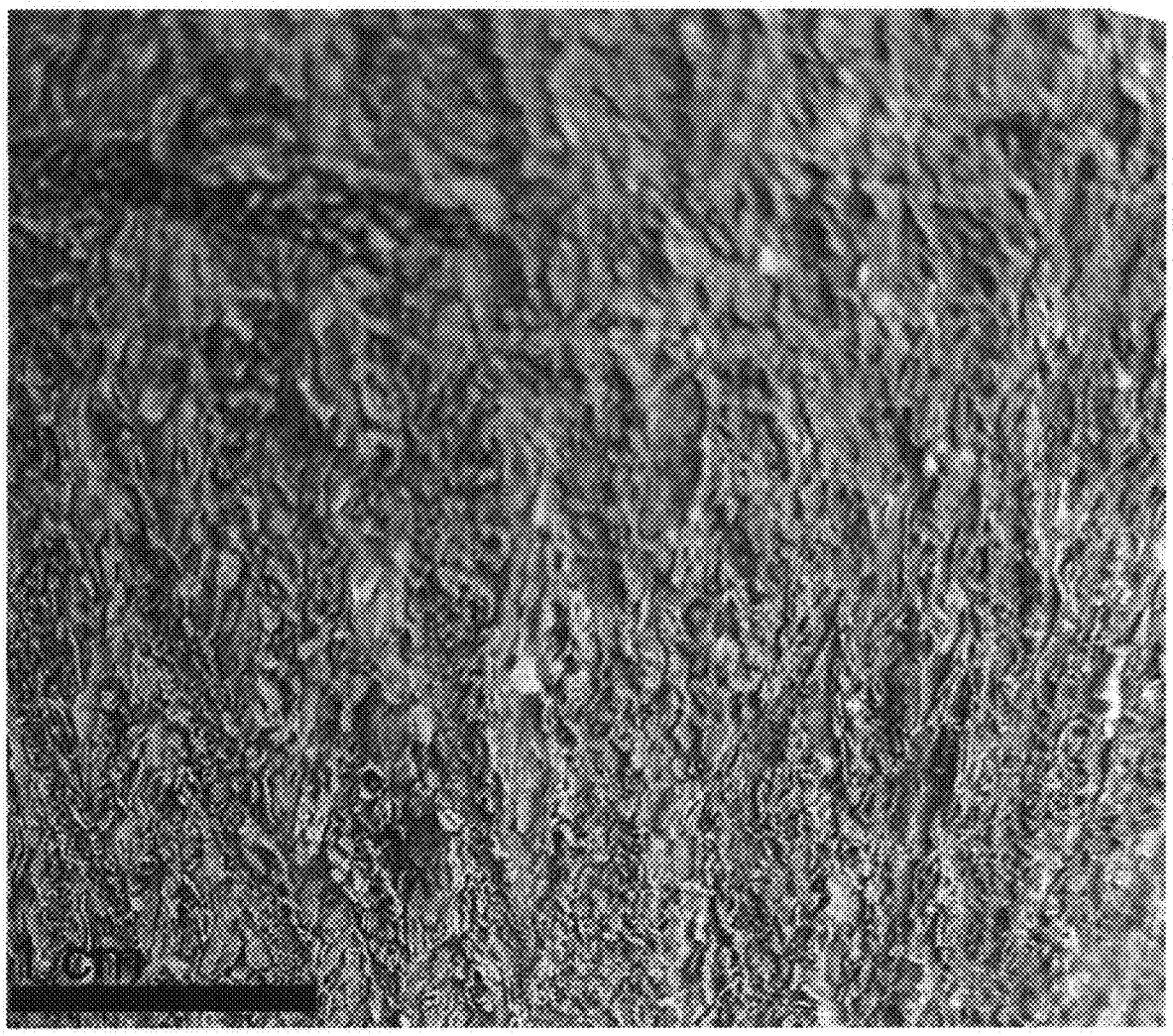
FIG. 2 is a color photograph of a section of bark.

*Bark*.—Dark brown soft texture bark (RHS 165A) with dark brown (RHS 200A) to black (RHS 186A) veins (FIG. 2).

Figure 20:
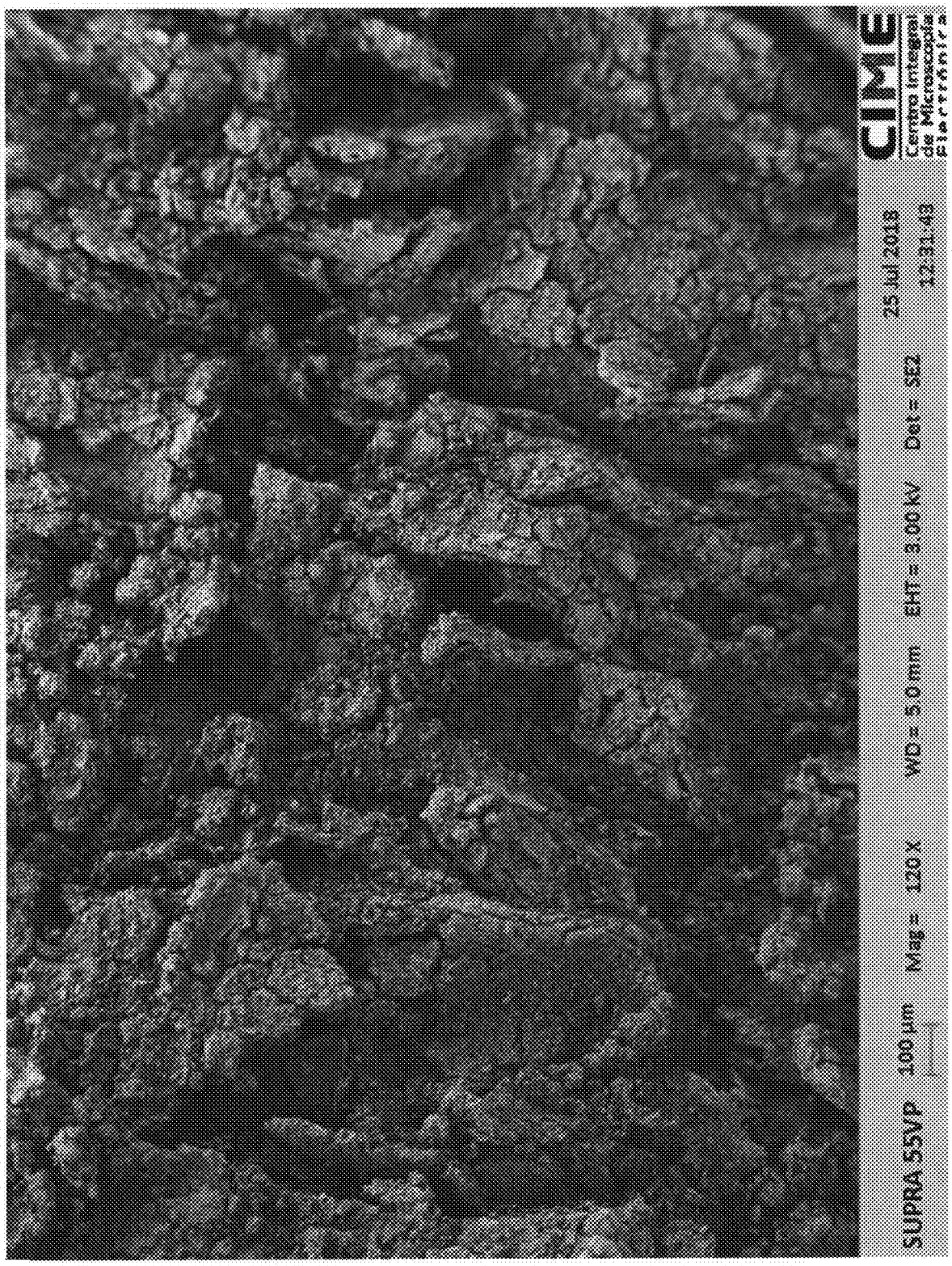
FIG. 20 is a black and white microphotograph of lenticels in the bark.

*Lenticels*.—Scarce evidence of lenticels of approximately 1 mm, dark brown (RHS 200A) to black (RHS 186A) color, and several in number (2 to 4/cm$^2$) (FIG. 20).

Branches:

*Canopy*.—Spherical somewhat irregular canopy, with open branches at the center.

*Length of branches*.—The fruit branches located one meter above the rootstock measure 1.8±0.54 m in length by 12.5±9.19 cm in diameter in their middle section,

*Angle of branches*.—Acute to straight angles of divergence (35.23° to 90.07°) with respect to the stem.

*Color of branches over* 2 *years old*.—Branches over 2 years old have a color similar to the dark brown stem (RHS 165A) with dark brown (RHS 200A) to black (RHS 186A) veins.

*Color of branches less than* 2 *years old*.—Younger branches of less than 2 years not lignified have green color RHS139C to RHSC 137C.

Figure 8:
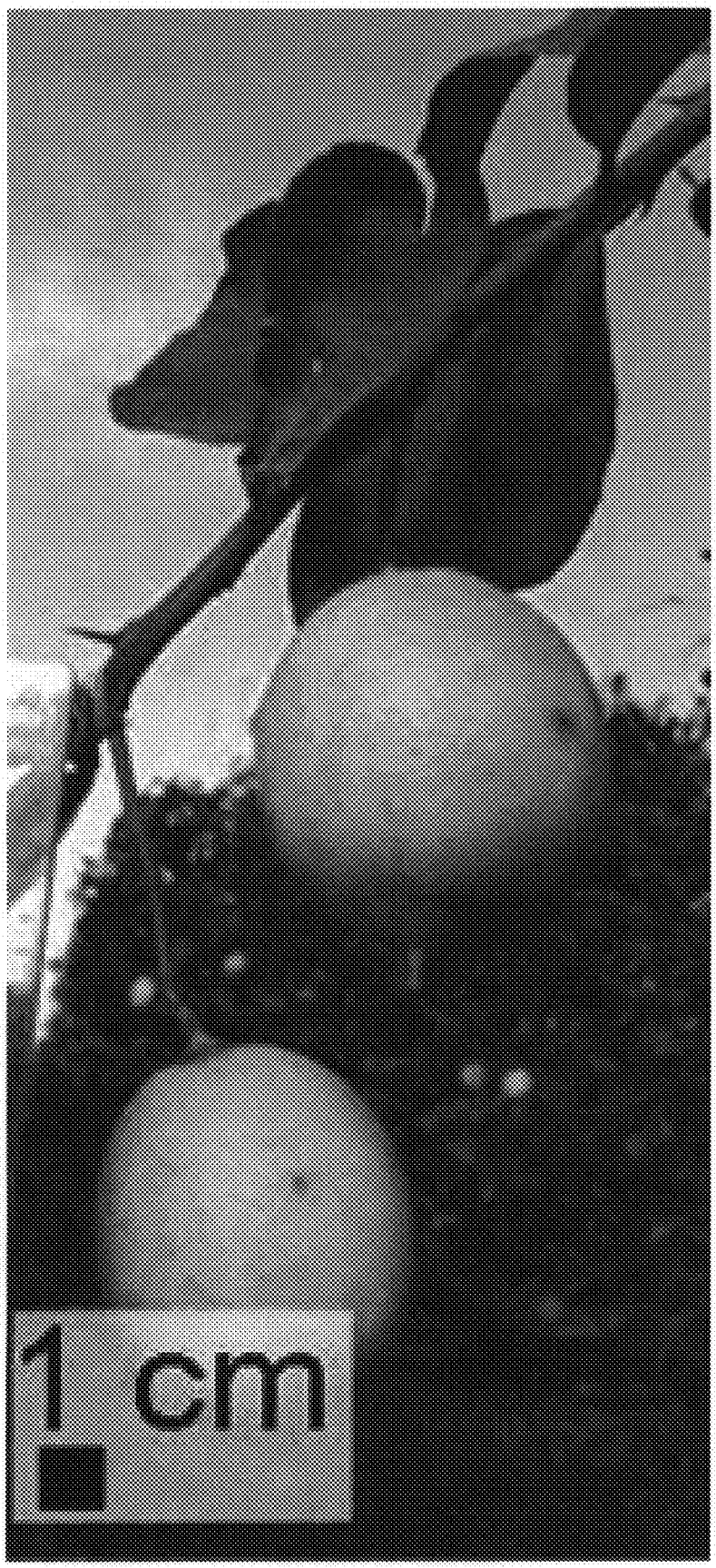
FIG. 8 is a color photograph of a branch with thorns and fruit.

*Thorns*.—Present. Straight thorns 1.75±0.88 cm long, present in a density of 0.6 to 0.3/cm$^2$ (FIG. 8).

Leaves: The specimens have simple leaves that are notophyllic (approximately 33.08±8.78 cm$^2$).

*Length*.—10.43±2.25 cm.

*Width*.—5.54±1.11 cm wide (having a length/width ratio 1.87).

*Color*.—Dark green blades (RHS 137A) are found on the upper surface and light green blades (RHS 146C) are found on the underside.

*Shape*.—Alternating, membranous, smooth, symmetrical elliptical shape in their middle section.

*Base*.—Obtuse to acute base (angle 92.82° to 58.61°) that is wedge-shaped, decurrent, and symmetrical, with a crenated edge.

Figure 3:
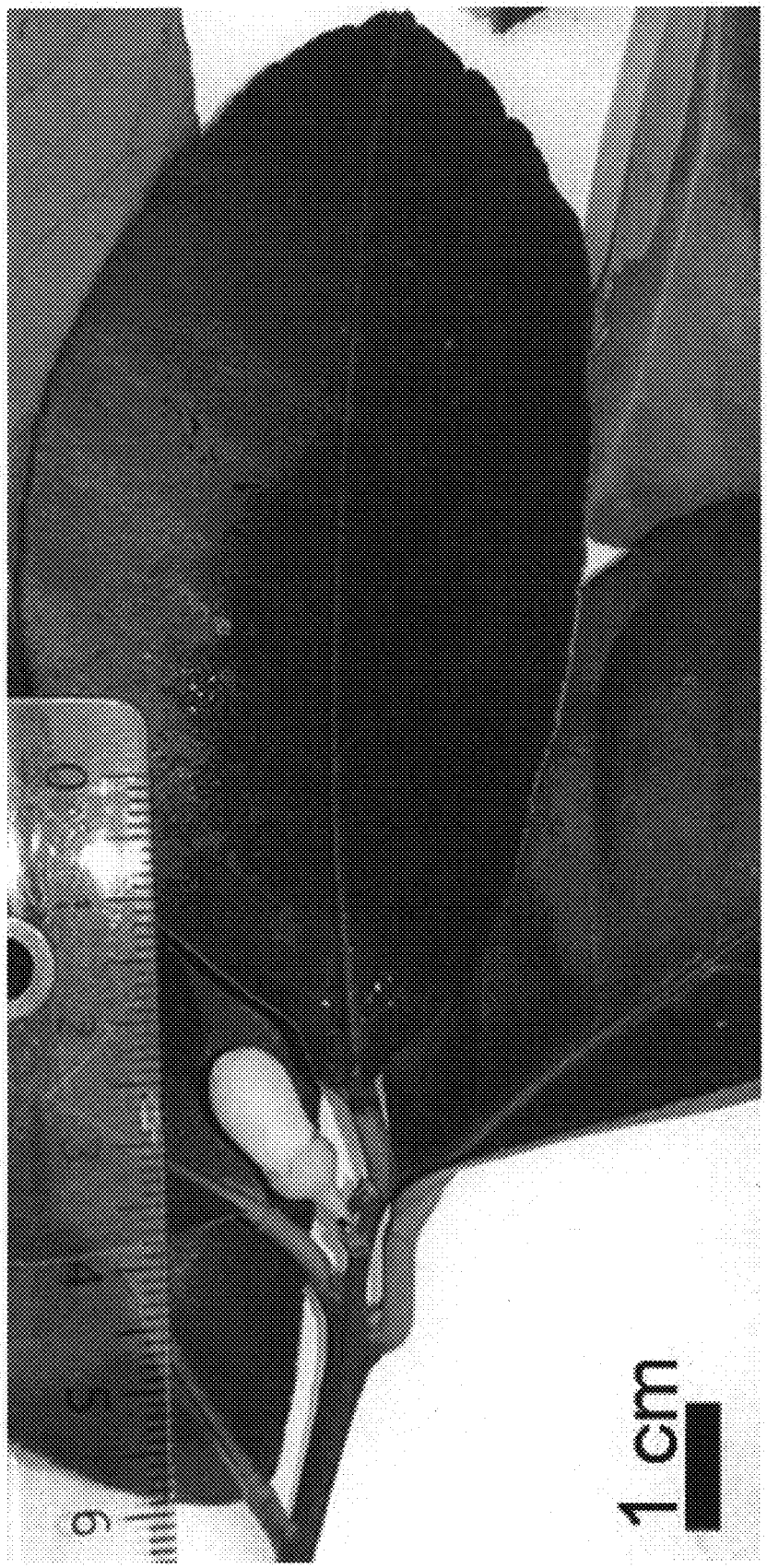
FIG. 3 is a color photograph of a young branch with leaves and terminal floral bud.
Figure 9:
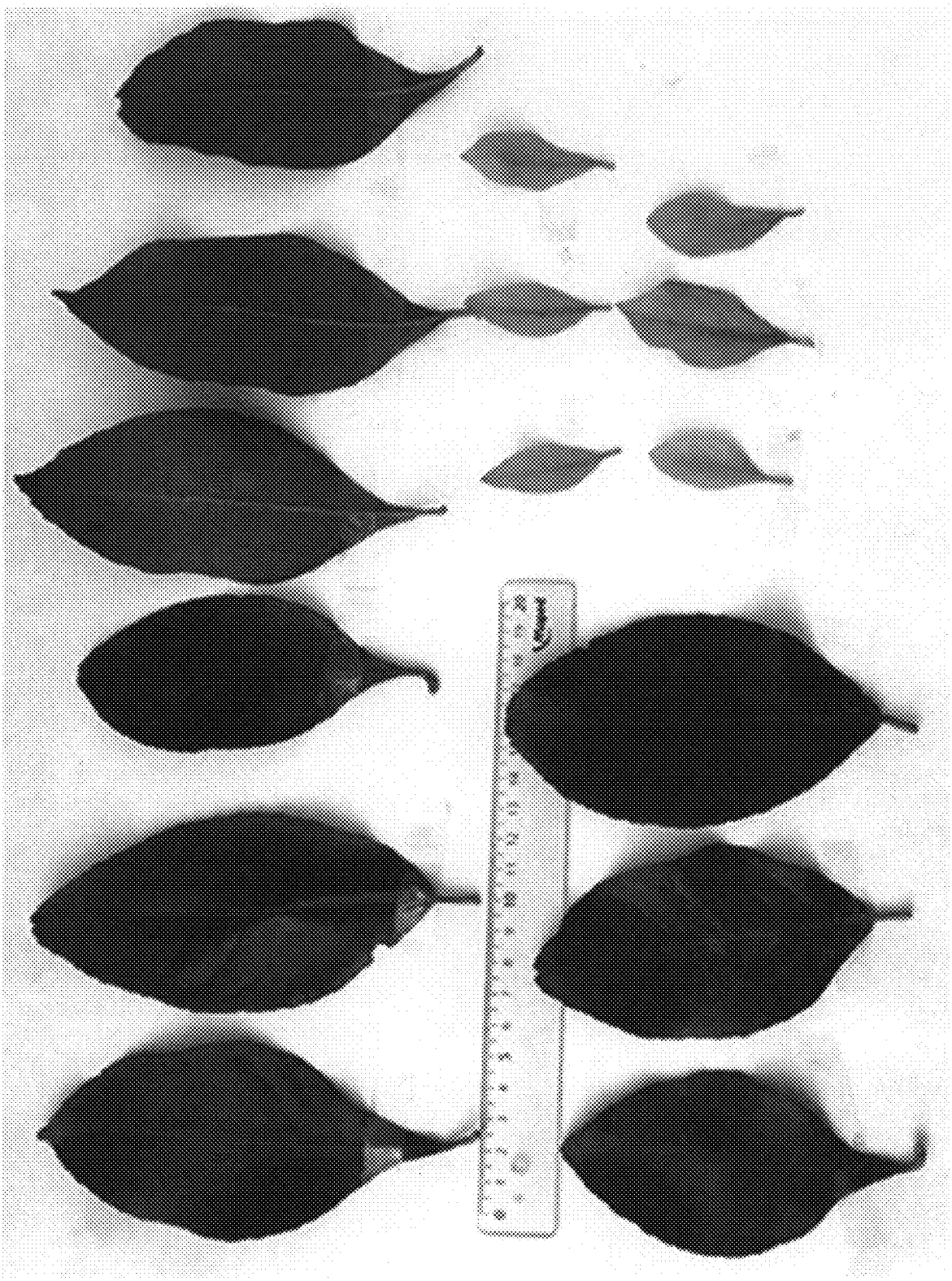
FIG. 9 is a color photograph of several leaves.

*Apex*.—Acute to obtuse apex (angle 80.33° to 143.24°), generally straight to shortly acuminate, occasionally rounded or retuse (slightly emarginated), in the latter case it seems to be associated with the activity of herbivorous insects (FIGS. 3 and 9).

Figure 10:
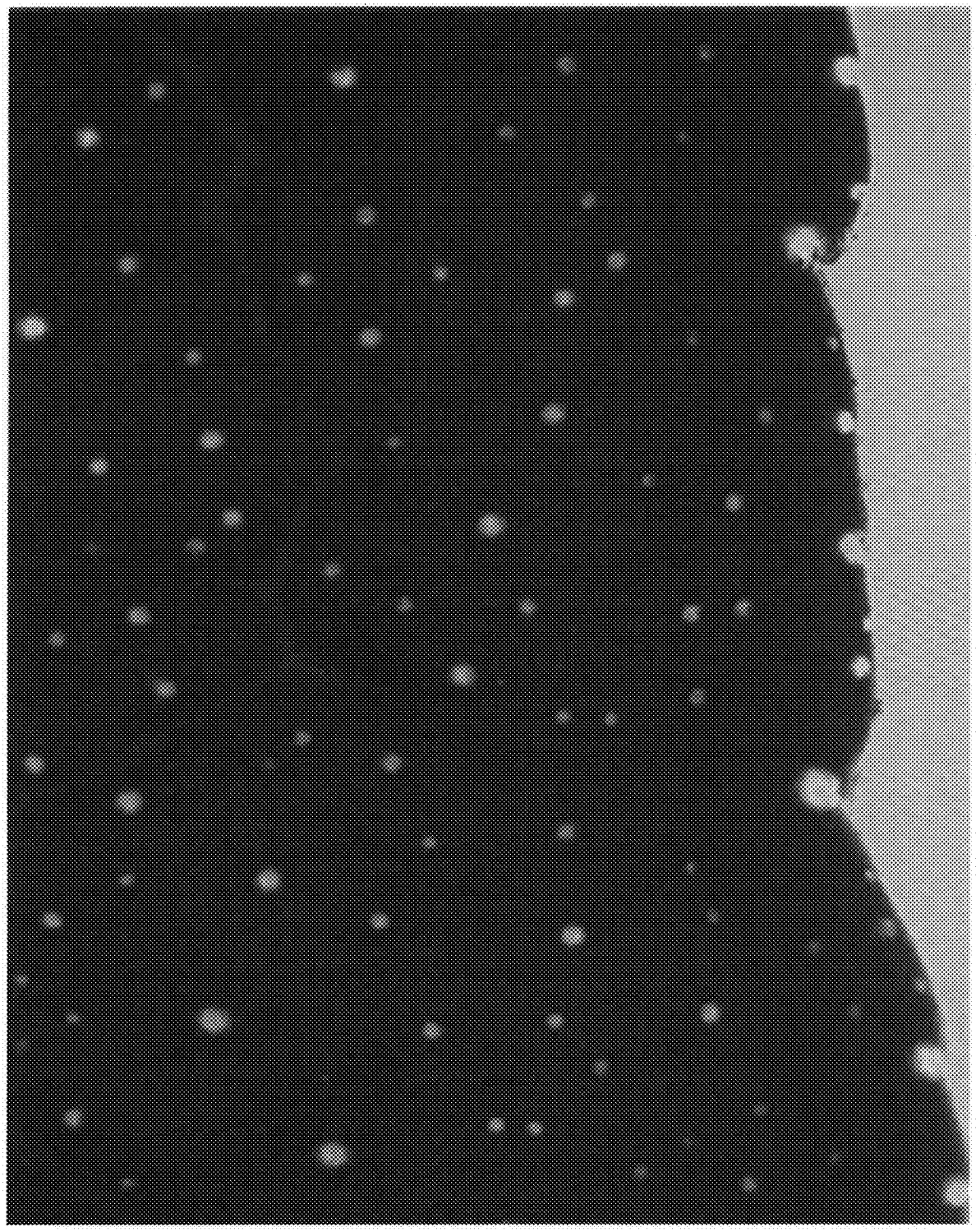
FIG. 10 is a color photograph of a leaf showing essential oil glands of a leaf.
Figure 21:
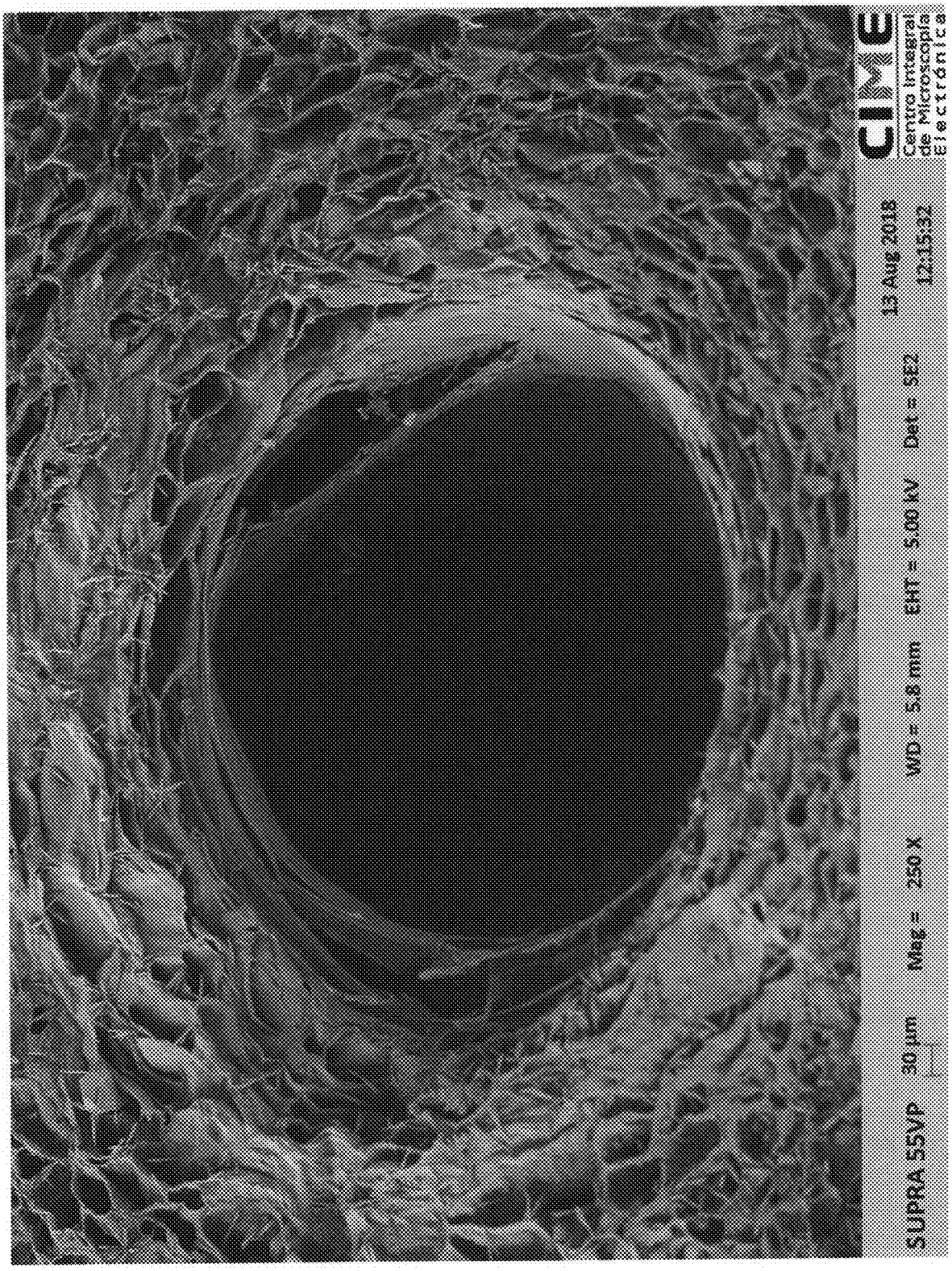
FIG. 21 is a black and white microphotograph of an essential oil gland.

*Essential oil glands*.—Translucent, distributed on the surface and leaf margins, with a density 1-2/mm$^2$, diameter 139.40±25.72 μm, with larger dimensions in the recesses of the margin of the blade (diameter 275.22±45.69 μm) (FIG. 10) (See also FIG. 21).

*Color*.—Coloring of anthocyanins in young leaves is absent; they display a greenish yellow color (RHS 145A) in the upper surface and greenish yellow (RHS 145B) on the underside (FIG. 9).

*Petioles*.—Wings: Unwinged. Color: dark green (RHS 137A), in section terete to subterete with adaxial ribs of scarce development. Length: 1.10±0.26 cm in length. Diameter: 1.66±0.26 mm in diameter in the dorsiventral plane of its middle section (FIG. 9).

*Veins*.—Pinnated eucamptodromous brochidodromous venation, with a single primary vein that is straight unbranched. Color: green (RHS 136A). Width at 1 cm from the apex: 0.23±0.5 mm. Width at the base 1 cm from the junction with the petiole: 1.40±0.21 mm.

Figure 4:
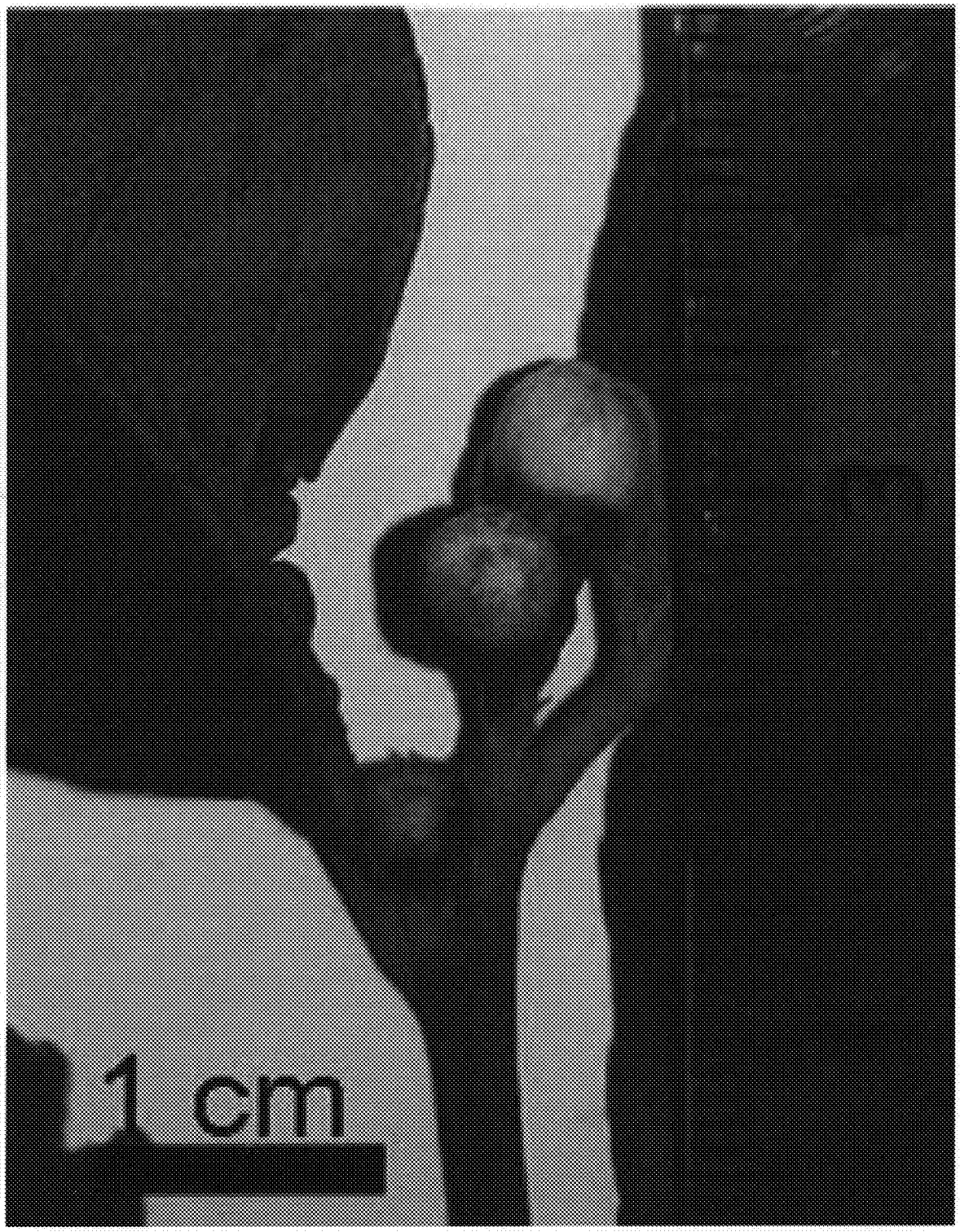
FIG. 4 is a color photograph of floral buds to terminal pairs and solitary axillary.

Flowers: Flower buds, alone or in groups of 2-3, terminal or axillary, are observed (FIGS. 3 and 4).

*Floral bud*.—Shape: oval. Length: 12.75±2.24 mm. Diameter: 6.18±1.05 mm in diameter in its middle section. Color: white (RHS 155D), with dark pink (RHS 53C) to pink spots (RHS 64D).

*Calyx*.—Gamosepalous dome-shaped calyx having 5 sepals (segments). Color: yellowish green (RHS 149C), Length: 8.18±0.94 mm. Width: 5.45±0.54 mm in width in each segment.

Figure 5:
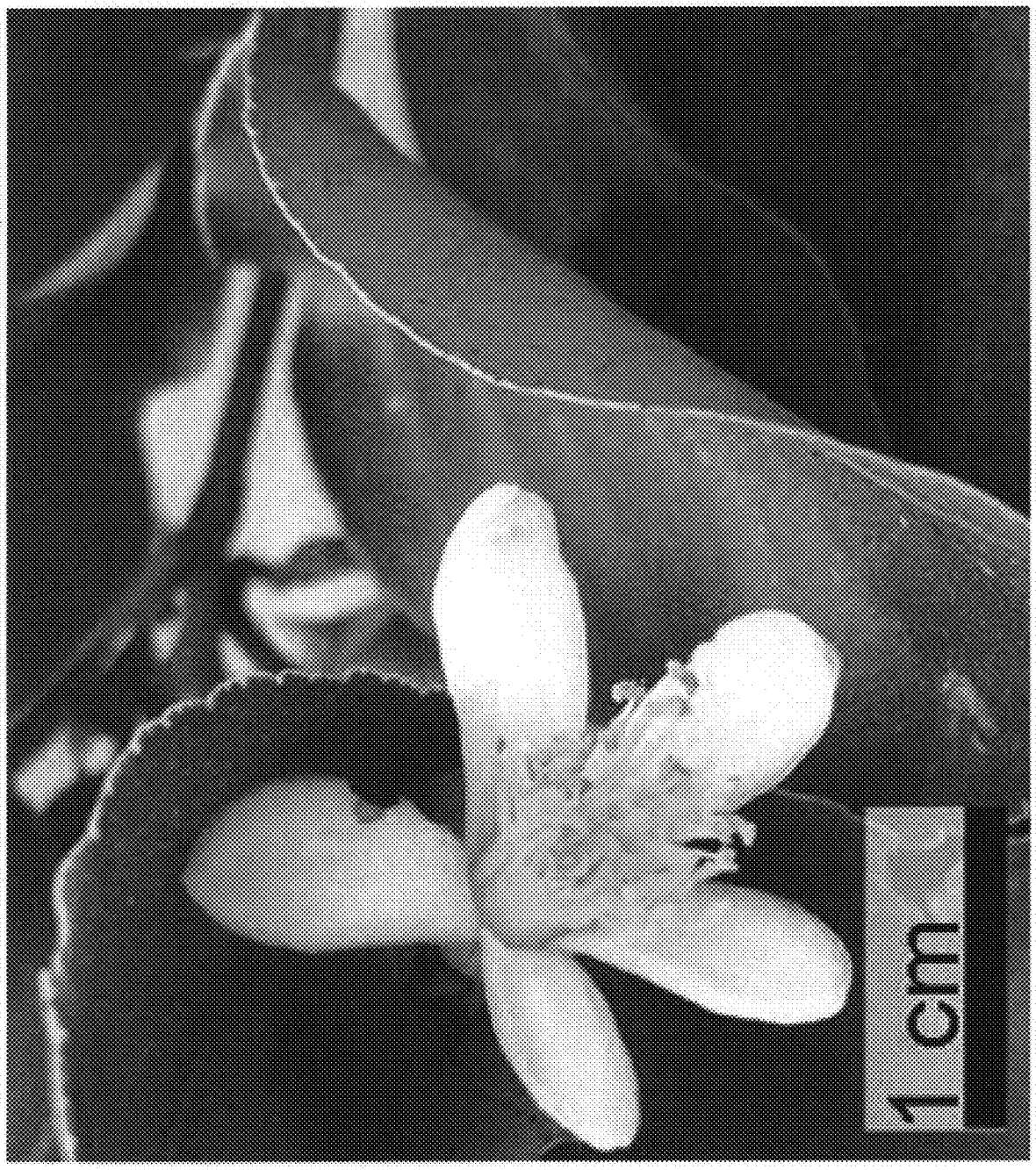
FIG. 5 is a color photograph of a fully open flower.

*Flowers*.—Perfect hermaphrodite flowers. Diameter when fully open: 3.02±0.19 cm (FIG. 5). Aroma: orange blossom.

*Pedicel*.—Brief. Color: light green (RHS 140D). Length: 0.54±0.05 cm. Diameter: 0.14±0.05 cm.

Figure 6:
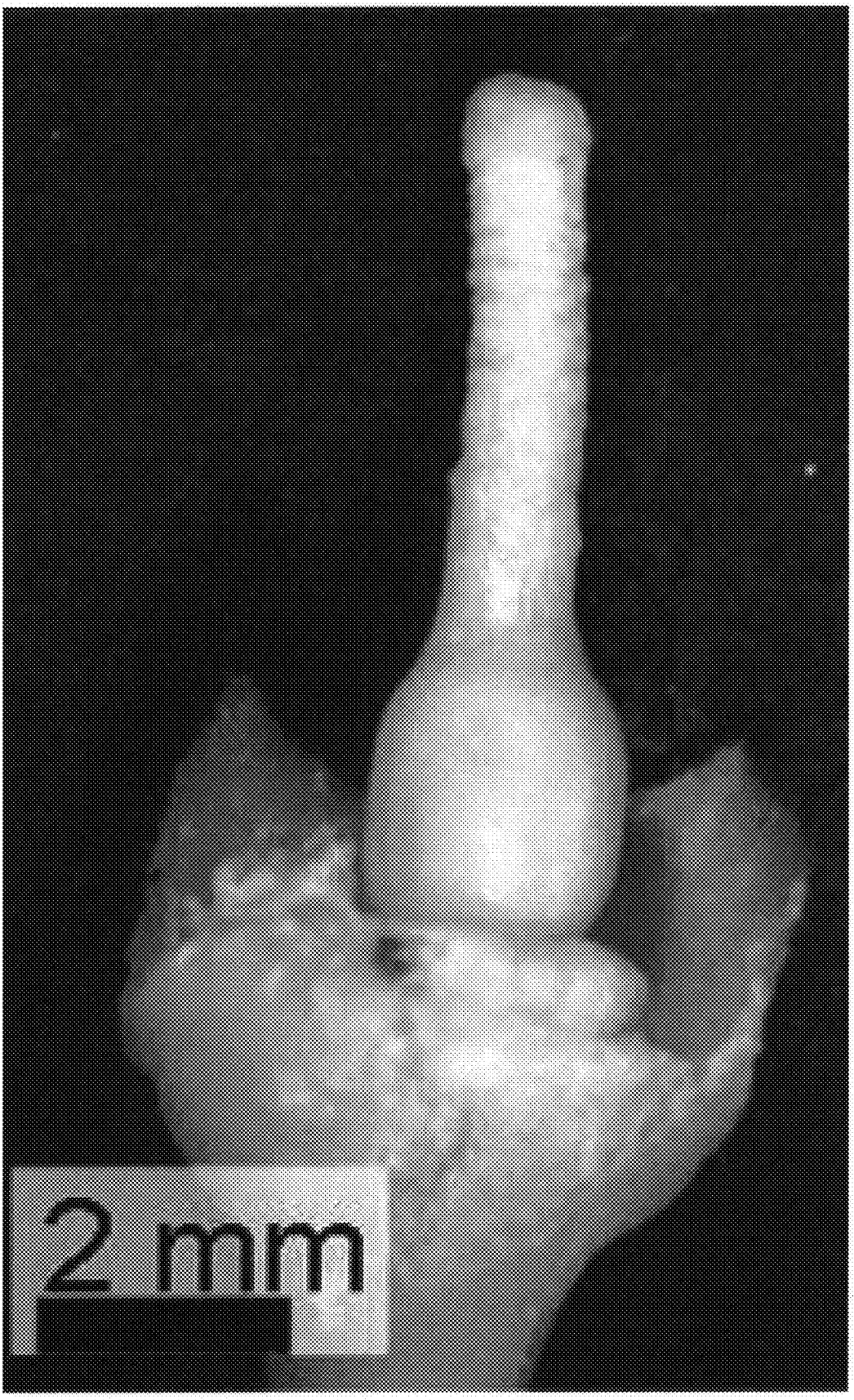
FIG. 6 is a color photograph of a gamosepalous calyx and gynoecium on a nectariferous disc.

*Sepals*.—Gamosepalous dome-shaped calyx has 5 sepals, acuminate. Apex: acute apex (RHS 149C). Length: 9.17±0.83 mm. Width: 5.57±0.54 mm in each segment (FIG. 6).

*Petals*.—Dialypetalous corolla has 5 petals. Shape: elliptic elongated oblongs in arches. Apex: acuminate to rounded, acute apex. Margin: smooth. Color: white (RHS 155D). Surface area: 0.66±0.11 cm$^2$. Length: 1.95±0.27 cm. Width: 0.64±0.10 cm.

*Pistil*.—Gamocarpellary gynoecium, arranged on a nectariferous disk. Number of stigma: single capitated globose stigma. Stigma color: light yellow (RHS 20A). Stigma thickness: 1.23±0.42 mm. Stigma diameter: 1.60±0.43 mm. Style: single linear apical style. Style color: light yellowish towards the apex (RHS 4D) to purplish pink at the base (RHS 71B). Style length: 5.98±1.03 mm. Style diameter: 1.35±0.15 mm in its middle section. Ovary color: yellowish green (RHS 145C). Ovary position: superior. Ovary shape: spherical. Ovary length: 2.05±0.10 mm. Ovary diameter: 2.26±0.21 mm in diameter in its middle section (FIG. 6). Ovary Locules: In cross-section, ten locules were observed per ovary. Ovary ovules: numerous ovules of axial placentation.

Figure 7:
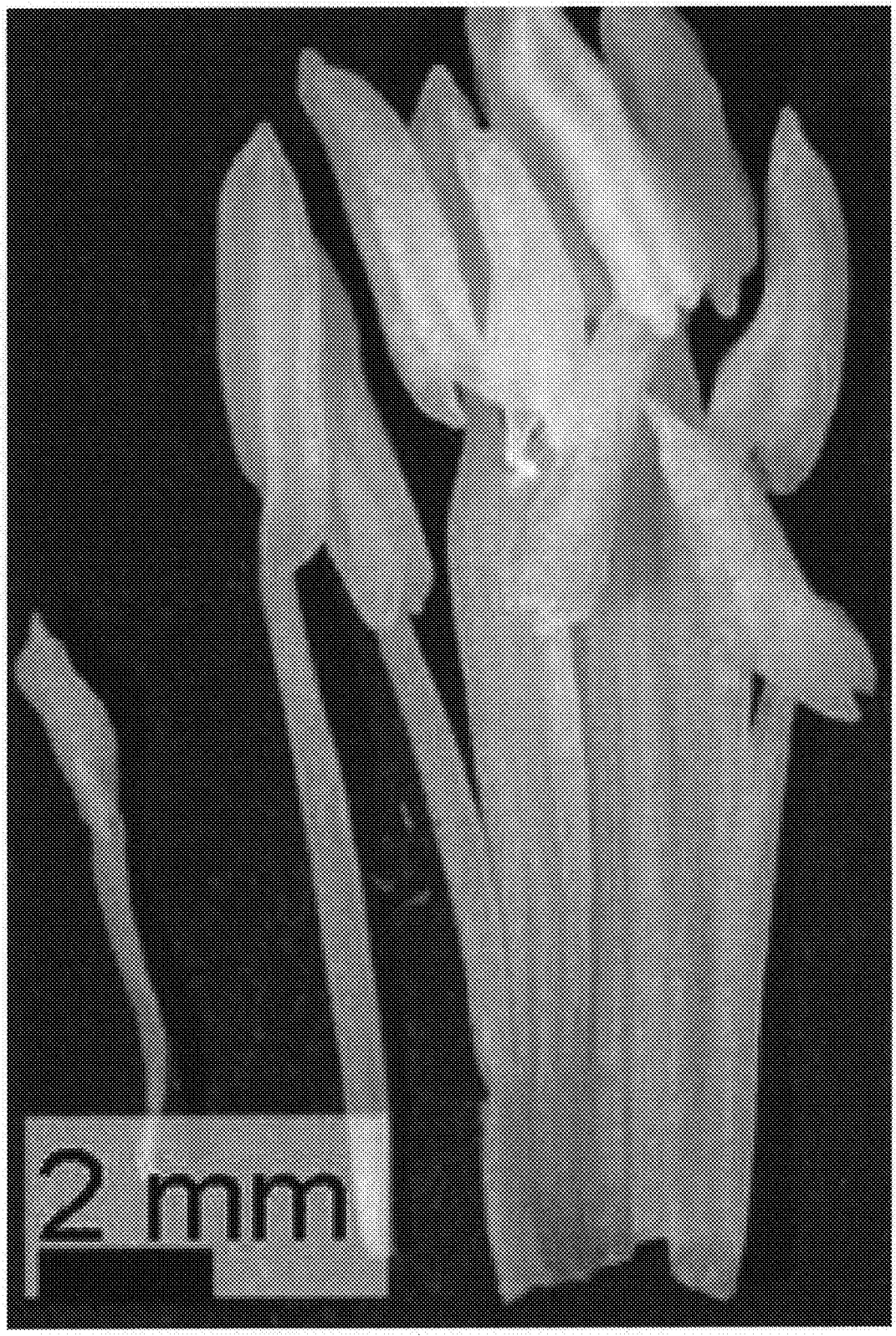
FIG. 7 is a color photograph of stamens wielded by the filament, free stamen, and staminode.

*Stamen*.—Polyadelphous androecium. Number: 43-56 stamens with 1-3 staminodes, in one or two cycles. Filaments: free or welded by 6-9 flattened filaments of 12.81±mm of total length. Anthers: Two-teaked. Anther color: light green (RHS 140D). Anther length: 2.3±0.2 mm. Anther diameter: 0.58±0.09 mm. (FIG. 7).

Fruit: Hesperidium. fruit are genuine, monothalamic, fleshy, indehiscent.

External characteristics.

Figure 11:
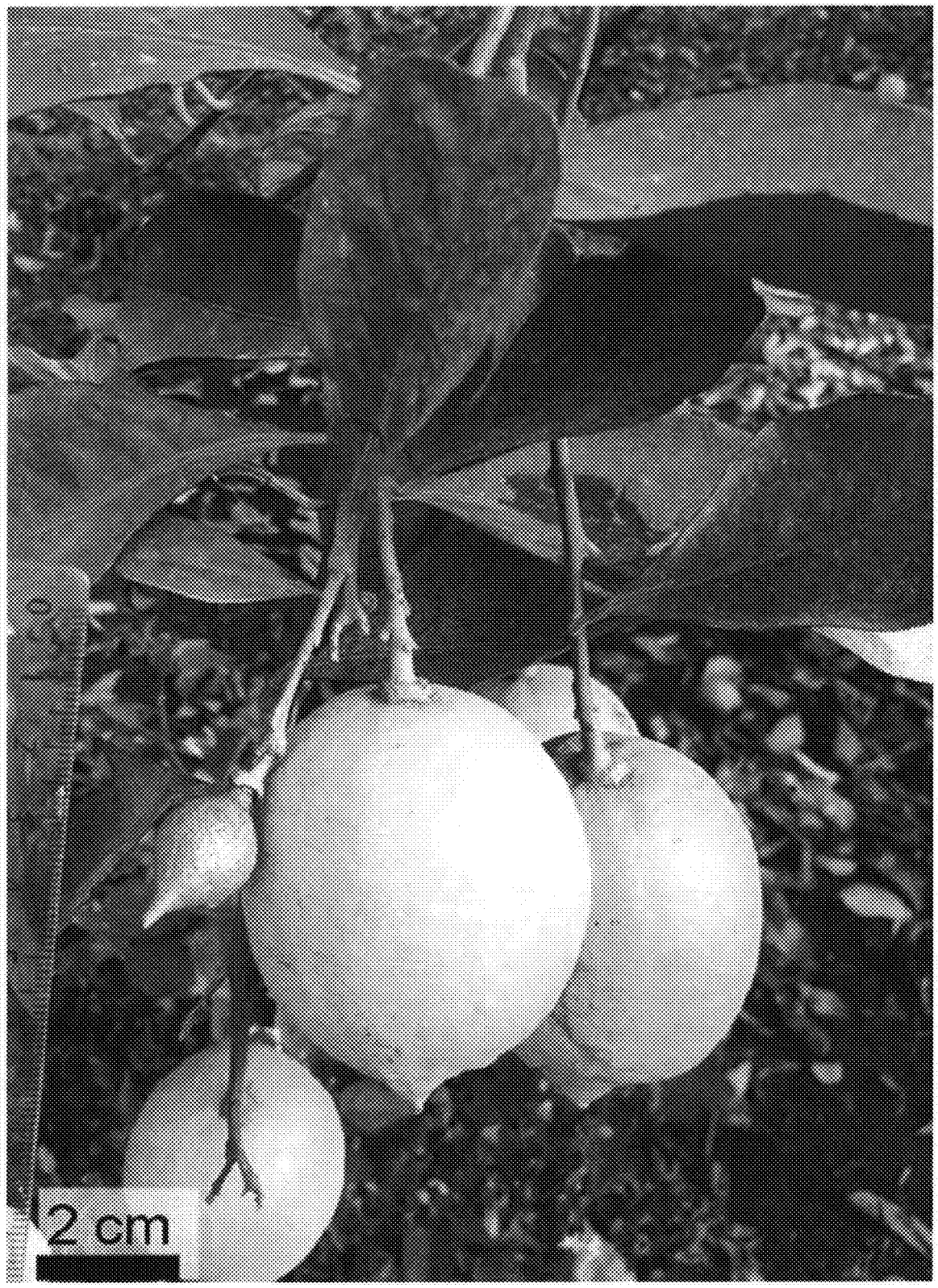
FIGS. 11 is a color photograph of a branch with fruits in various stages of maturity.
Figure 12:
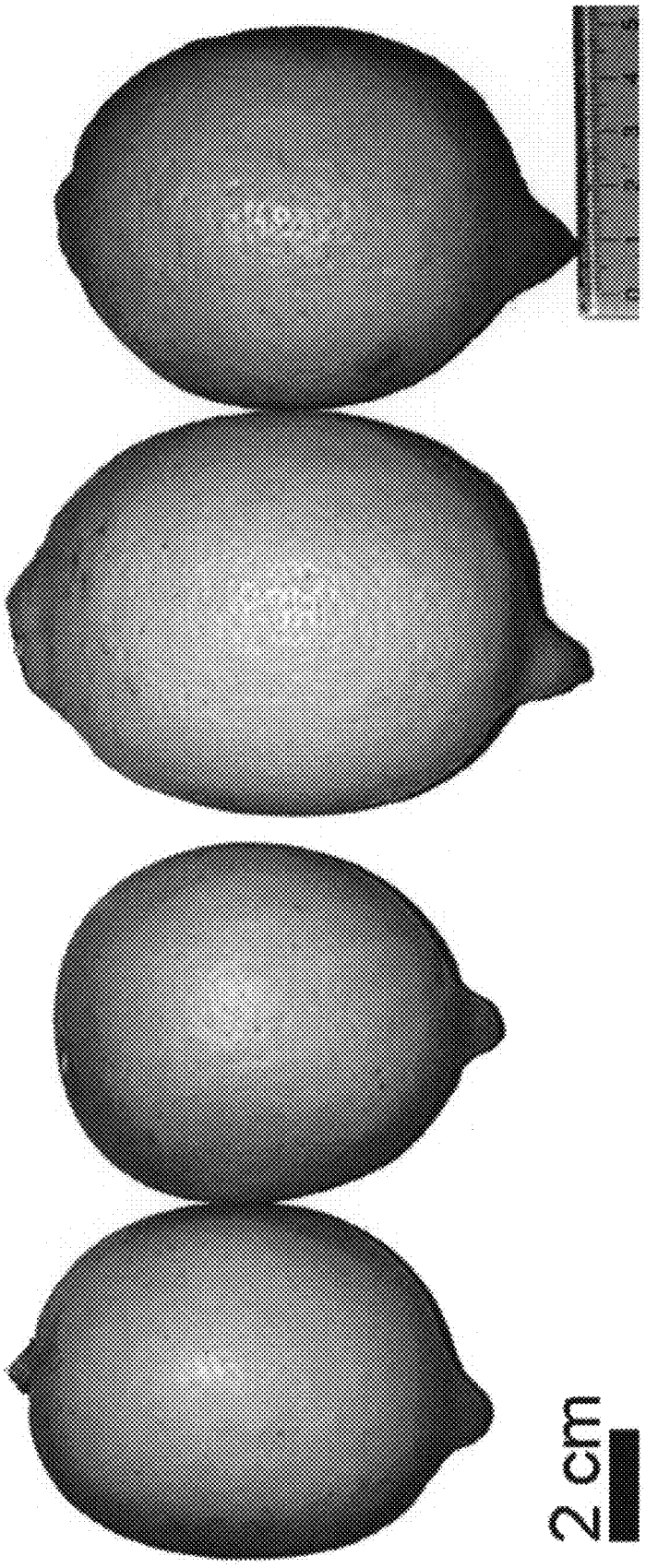
FIG. 12 is a color photograph of the morphological aspects of different fruits.

*Color*.—Yellow (RHS6A) with greenish yellow coloration at the end of the nipple (RHS149A) (FIGS. 11 and 12).

*Shape*.—Elliptic-oval shape. Length: 7.99±0.64 cm. Diameter: 5.99±0.60 cm in diameter in its middle section, where it has the largest diameter.

*Weight*.—Average weight 116.01±32.28 gr (FIG. 12).

*Base*.—Straight or with a short neck or collar (0.5±0.2 cm in length).

Figure 13:
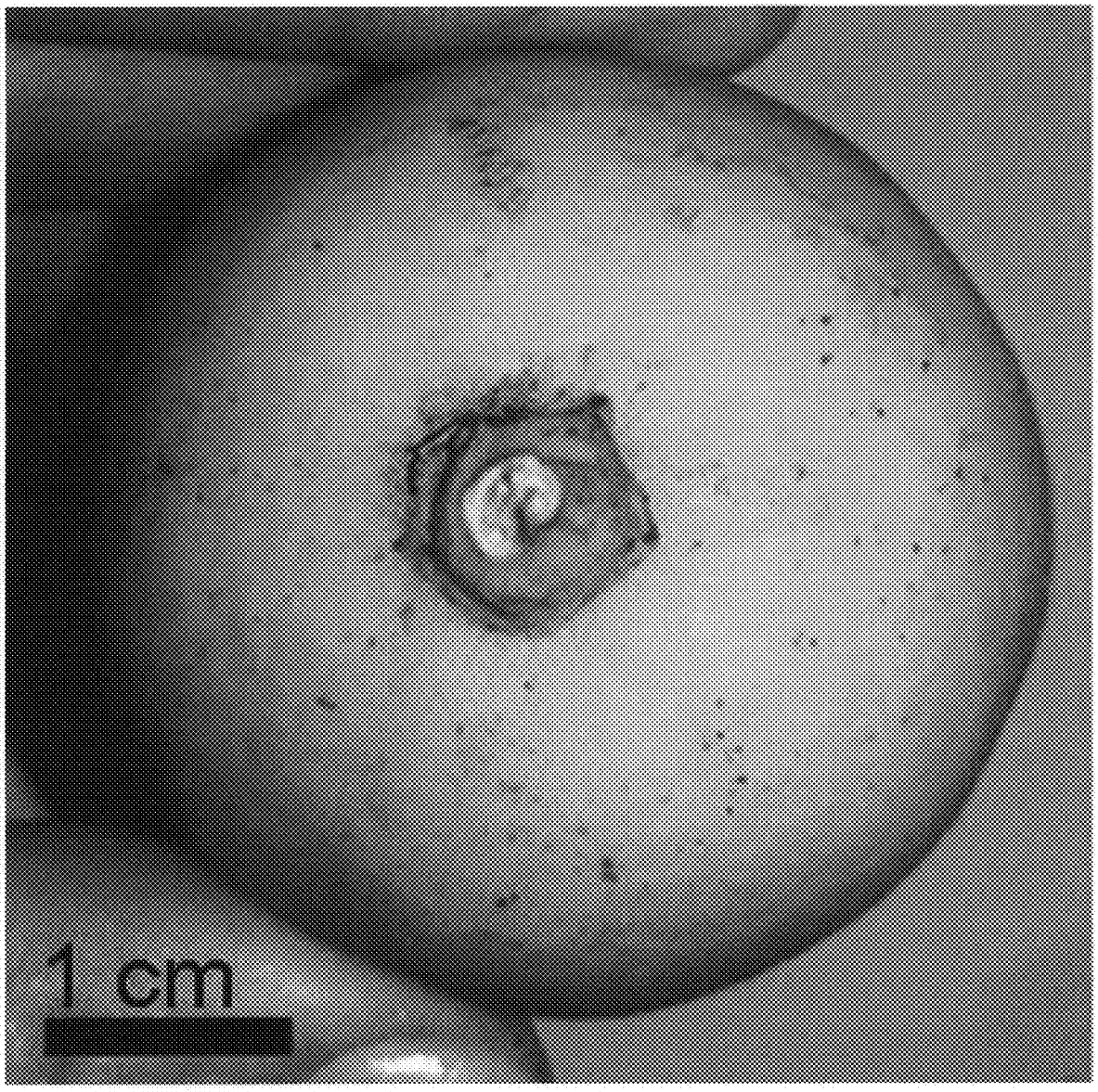
FIG. 13 is a color photograph of a straight base of a fruit with persistent calyx in the form of rudiment.

*Calyx*.—Persistent, in the shape of a rudiment (FIG. 13).

*Apex*.—Nipple-shaped protrusion of 1.03±0.21 cm in length by 1.33±0.24 cm in diameter is found at the base.

Figure 14:
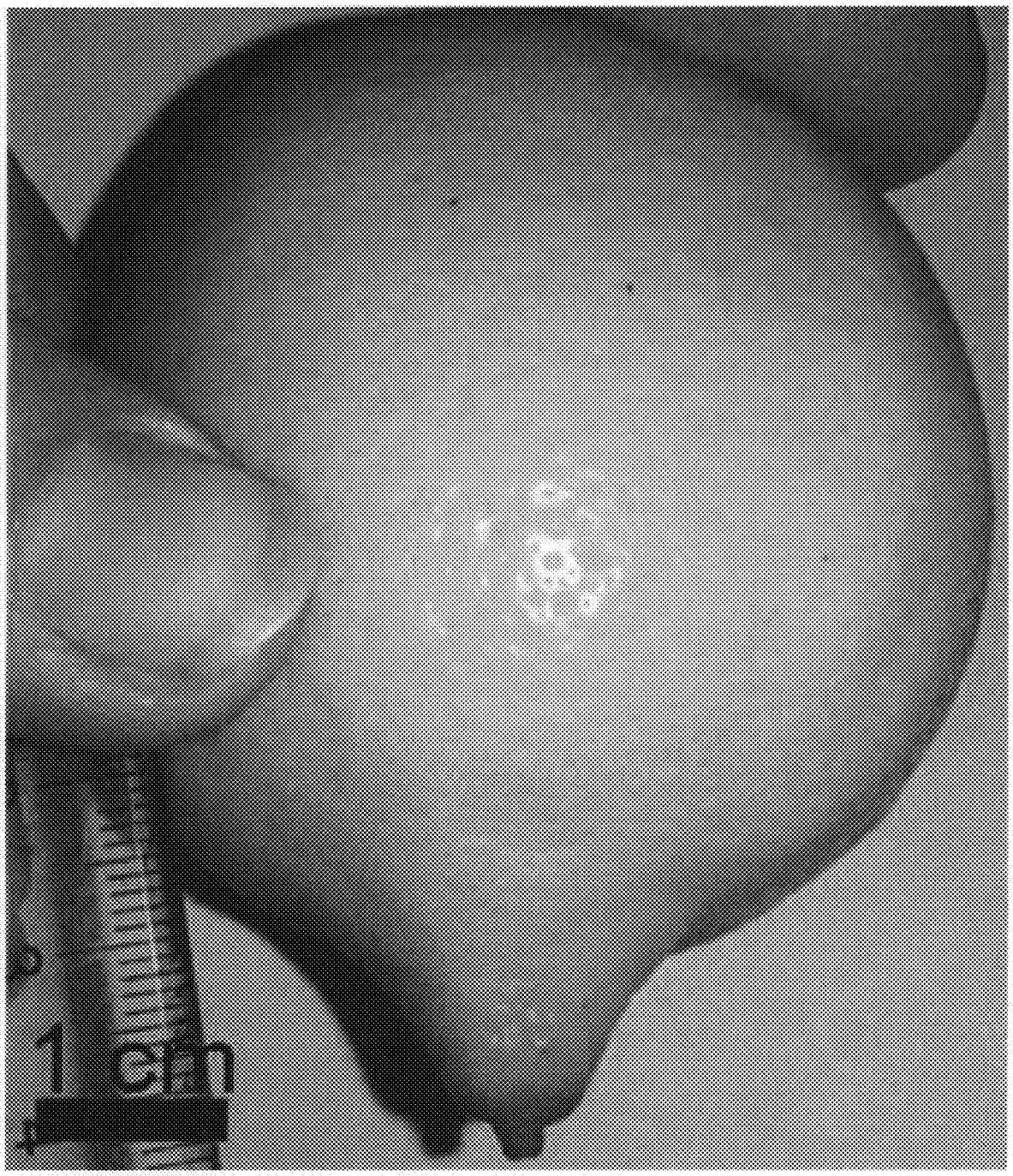
FIG. 14 is a color photograph of an apex with a nipple-shaped protuberance of a fruit with poorly defined areolar groove and the remains of a persistent style.

*Stylar scar*.—Less than 1 mm in diameter and sometimes with remains of persistent style (FIG. 14), frequently accompanied by an undefined areolar groove of 2.54±0.31 cm in diameter.

*Husk*.—Surface: smooth husk, evidently glandular. Thickness: 3.5±0.8 mm (flavedo and ectocarp 1.0-1.5 mm and albedo or mesocarp 1.7-3.3 mm). Glands: 520.81±137.16 μm in diameter. Gland density: average density of 60 glands/cm2. Color: yellow exocarp (RHS6A) and white mesocarp (RHS 155D) (FIGS. 15, 16, and 17).

Internal characteristics:

*Flesh color*.—Yellow (RHS12A).

Figure 15:
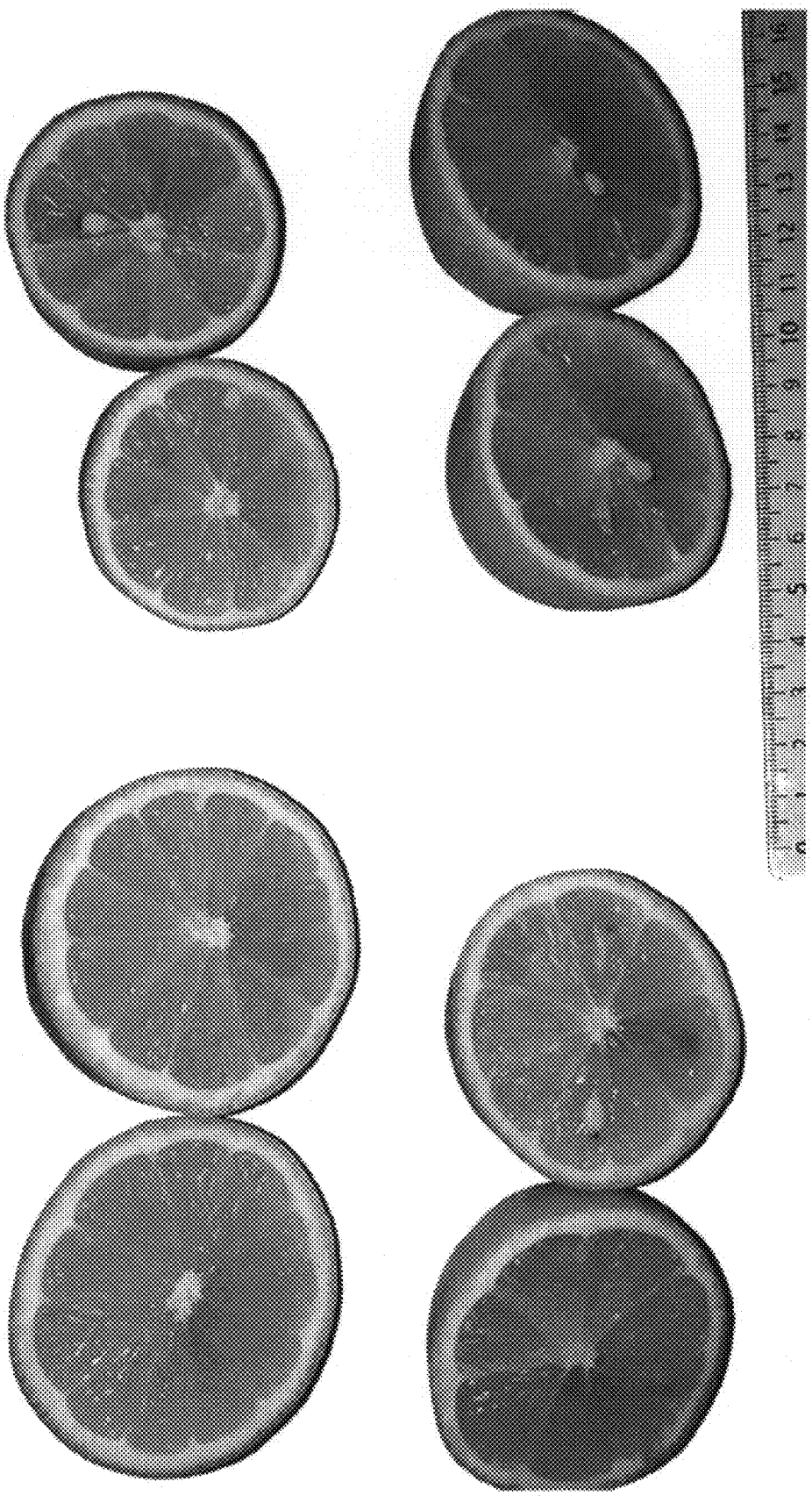
FIG. 15 is a color photograph of average sections of fruit.
Figure 16:
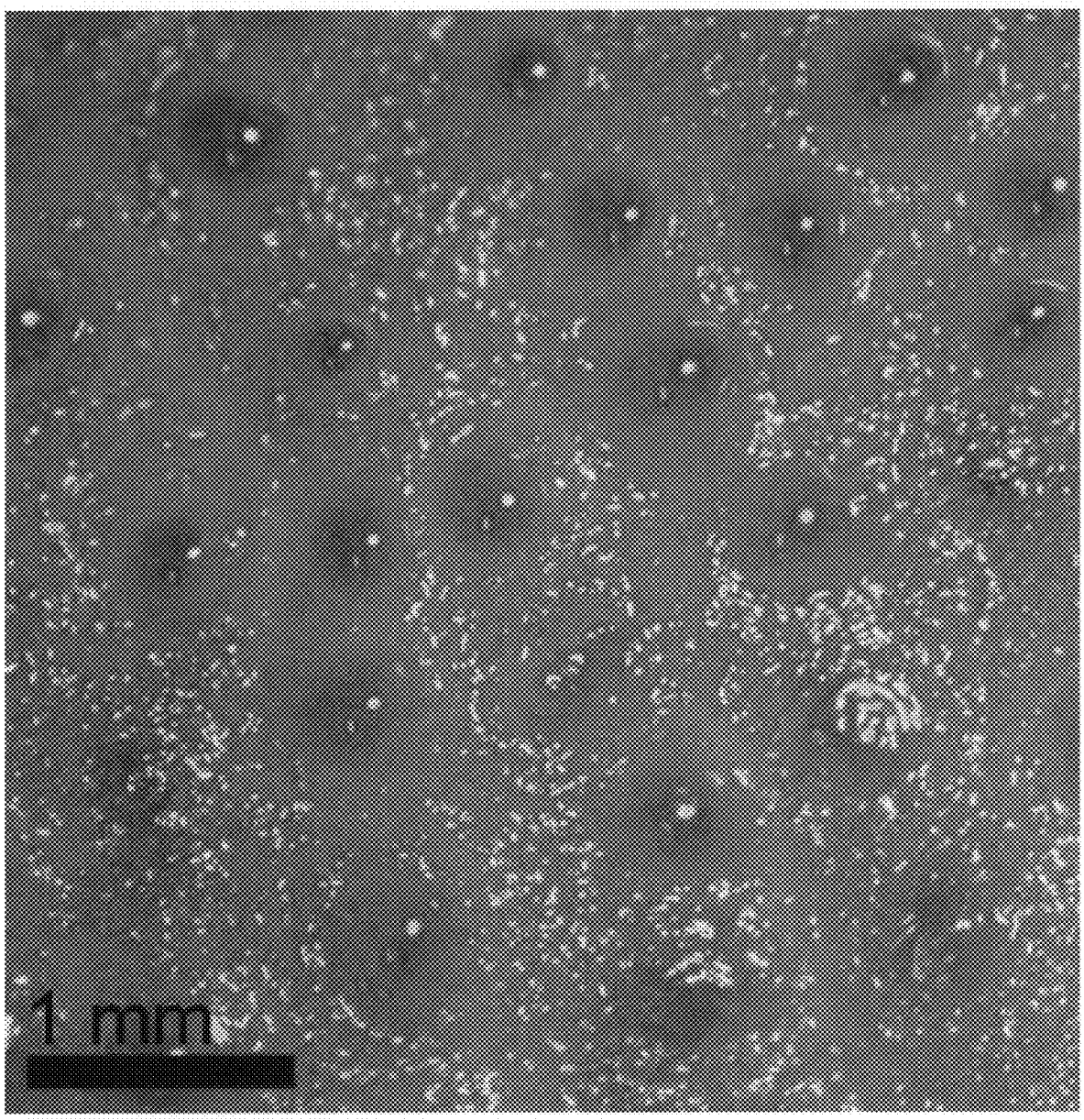
FIG. 16 is a color photograph of glands of essential oils present in the peel of a fruit.
Figure 17:
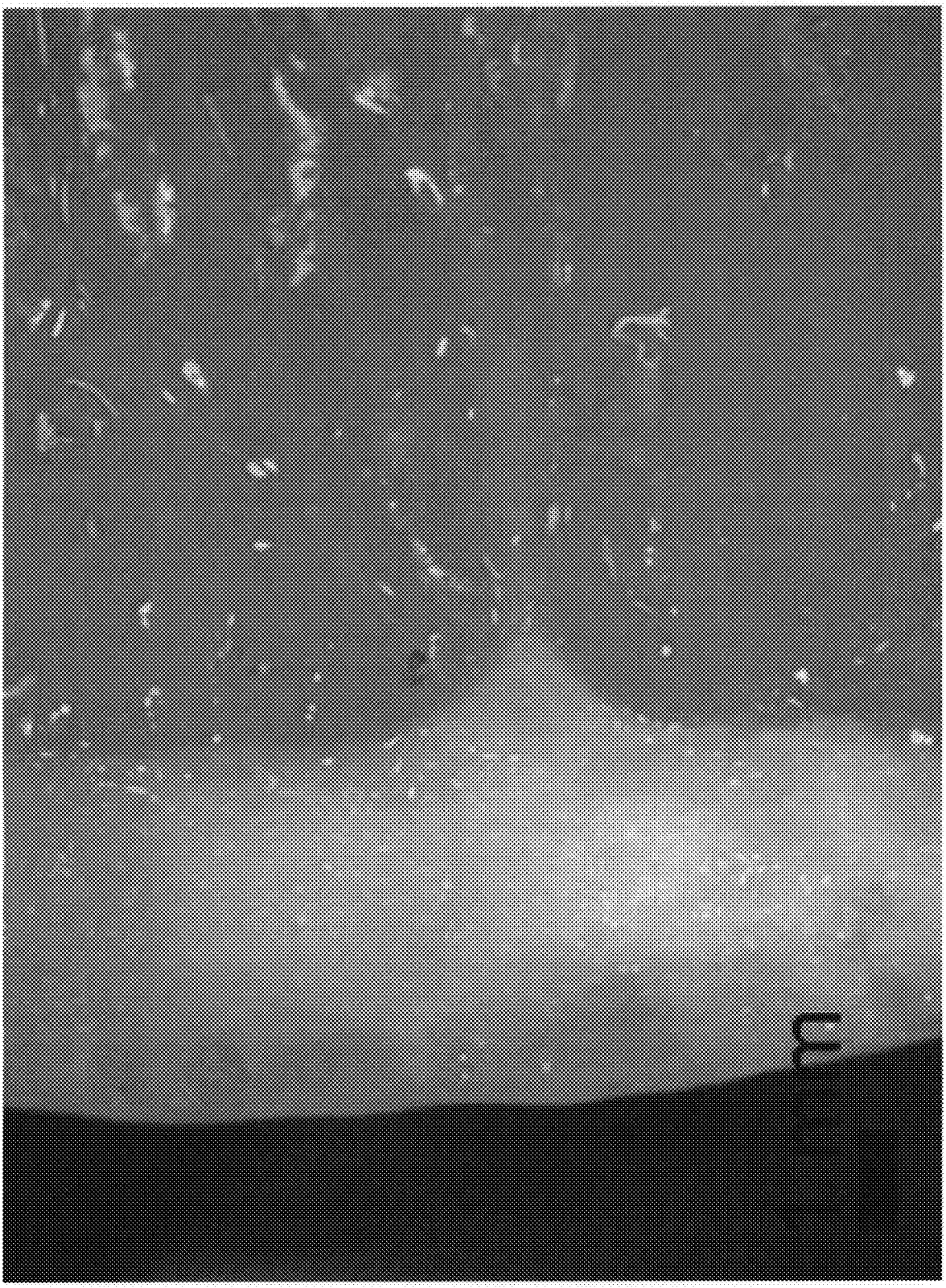
FIG. 17 is a color photograph of a cross-section of fruit where the flavedo (exocarp) and albedo (mesocarp) of the husk can be seen.

*Interior segments*.—9.29±1.04 (FIGS. 15 and 16).

*Interior segment membranes*.—Moderate resistance.

*Septa*.—Equal number as sgments. Thickness: 0.2 to 0.3 mm.

*Vesicles*.—Cylindrical. Length: 1.5±0.5 cm. Diameter: 0.26±0.05 cm in their widest section.

Figure 18:
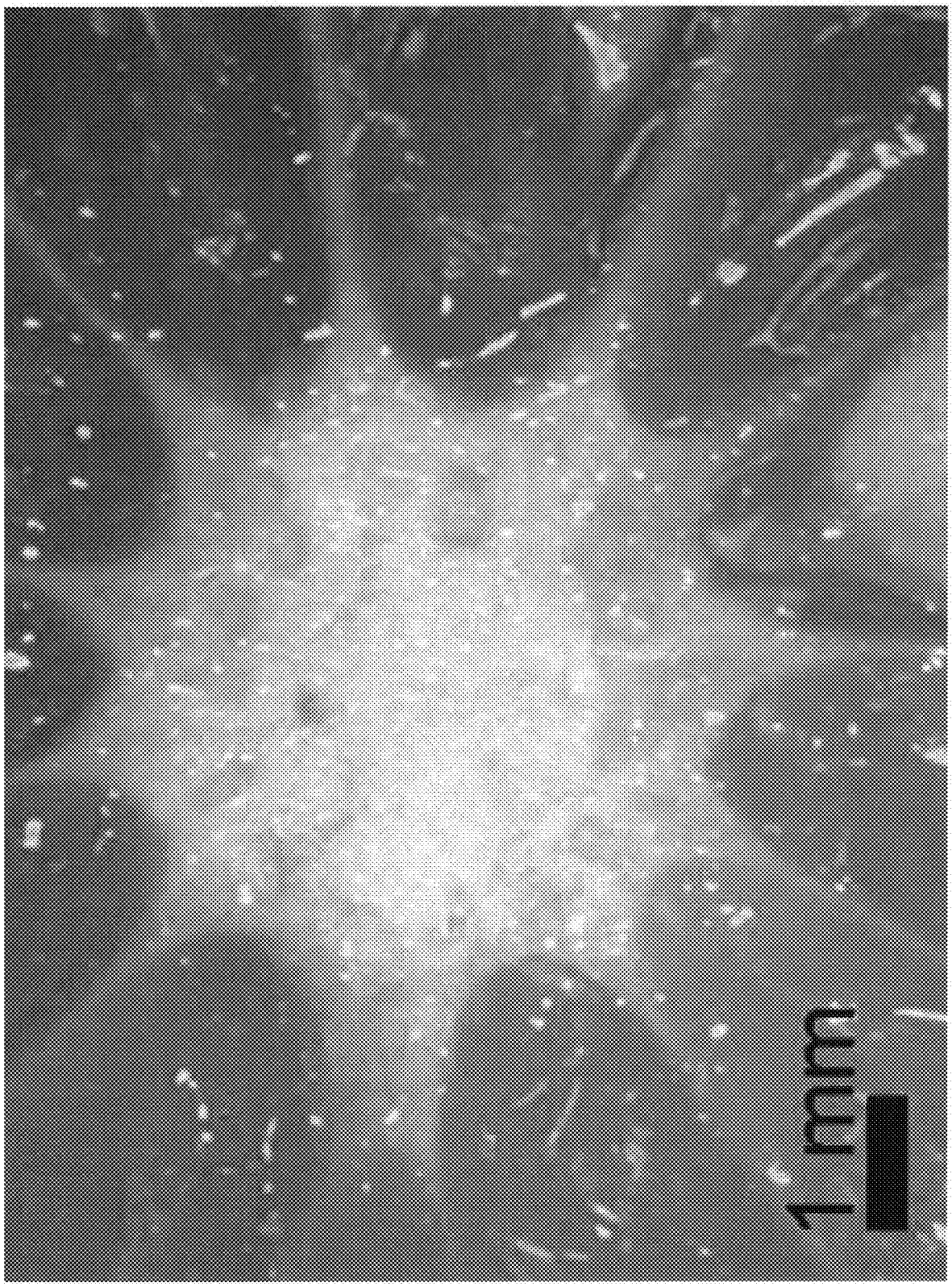
FIG. 18 is a color photograph of the axis of a fruit.

*Axis*.—Solid to semi-hollow. Diameter: 0.56±0.12 cm (FIG. 18).

Figure 19:
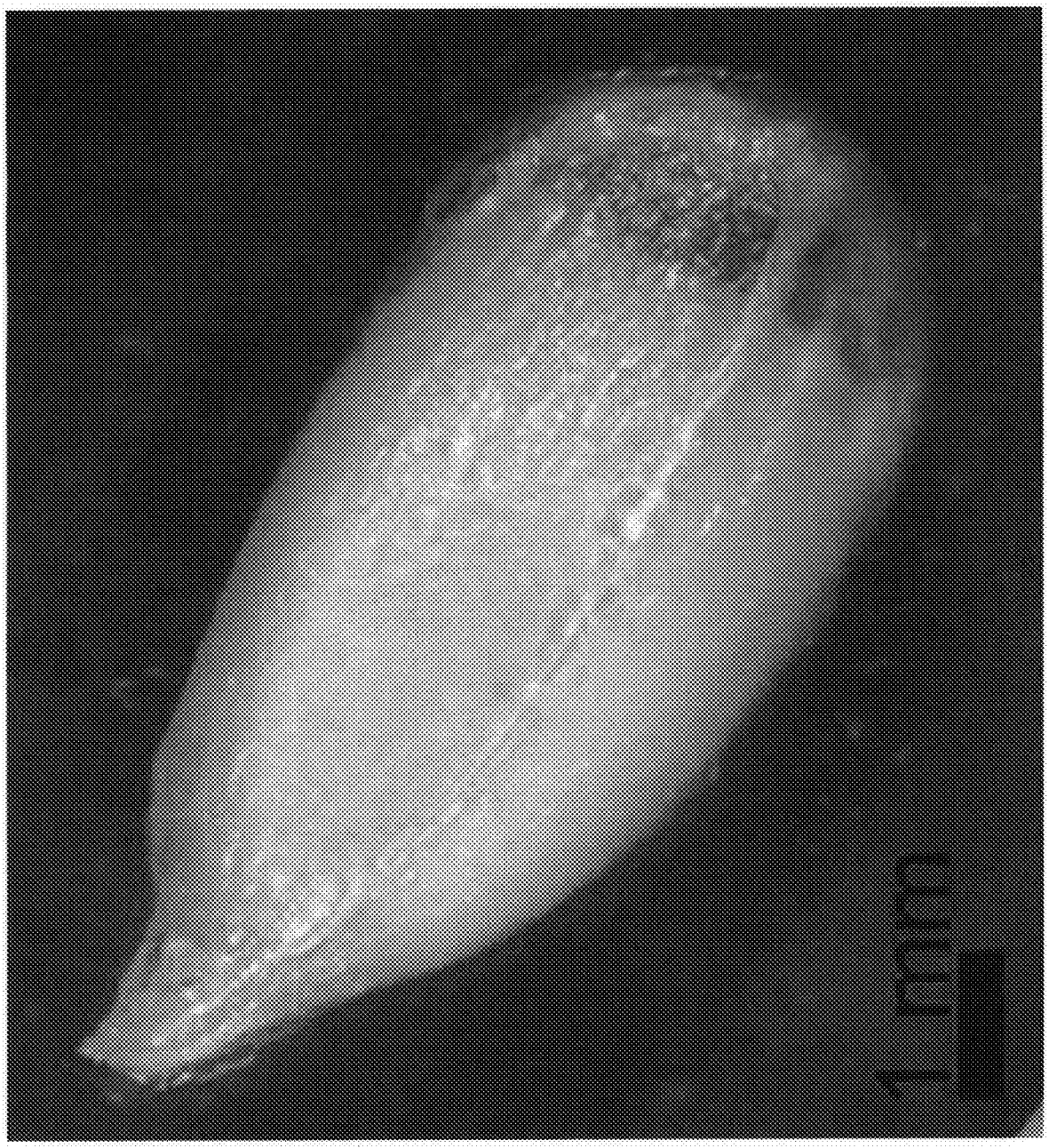
FIG. 19 is a color photograph of a seed of a fruit.

*Seeds*.—Each fruit has an average of 9.45±3.50 seeds of which 1-2 can be aborted. Length: 10.75±1.4 mm. Width: 5.75±0.66 mm. Shape: elliptical to ovate shape. Surface: smooth. Color: white (RHS155D) with a violet-pink collar at the base (RHSN77D) (FIG. 19).

*Juice*.—Color: yellow (RHS4A). Total sugars: 8.22±0.49° brix. pH: 5.51±0.09. Acidity: 0.054±0.10 equivalents of citric acid. Sugar-acid ratio: 150:1. Flavor: lemon.

| Plant | pH | ° Brix | mL of 0.1N NaOH | Percentage of citric acid** | Sugar:acid ratio |
|---|---|---|---|---|---|
| 1 | 5.62 | 8.9 | 0.8 | 0.051 | 174.5:1 |
| 2 | 5.55 | 8.3 | 0.9 | 0.057 | 145.61:1 |
| 3 | 5.44 | 7.9 | 0.8 | 0.051 | 145.9:1 |

-continued

| Plant | pH | ° Brix | mL of 0.1N NaOH | Percentage of citric acid** | Sugar:acid ratio |
|---|---|---|---|---|---|
| 4 | 5.46 | 7.8 | 0.9 | 0.057 | 136.84:1 |
| Average | 5.51 ± 0.09 | 8.22 ± 0.49 | 0.85 ± 0.05 | 0.054 ± 0.10 | 152.96 ± 16.14 |

**Percentage of citric acid: volume of NaOH used x 0.064.

We claim:

1. A new and distinct variety of lemon tree as described and illustrated called 'Glueck' that is characterized as producing fruit with a juice having a lemon flavor and a high sugar-acid ratio.

* * * * *